(12) United States Patent
Tsubata

(10) Patent No.: US 7,885,432 B2
(45) Date of Patent: Feb. 8, 2011

(54) BIOMETRIC INFORMATION MEASURING APPARATUS

(75) Inventor: Keisuke Tsubata, Chiba (JP)

(73) Assignee: Seiko Instruments Inc. (JP)

( * ) Notice: Subject to any disclaimer, the term of this patent is extended or adjusted under 35 U.S.C. 154(b) by 1113 days.

(21) Appl. No.: 11/600,559

(22) Filed: Nov. 16, 2006

(65) Prior Publication Data

US 2007/0116329 A1    May 24, 2007

(30) Foreign Application Priority Data

Nov. 24, 2005    (JP) .............................. 2005-338998

(51) Int. Cl.
*G06K 9/00* (2006.01)

(52) U.S. Cl. .................. 382/115; 382/124; 600/509

(58) Field of Classification Search ................ 382/115, 382/100, 124, 126; 600/509, 344
See application file for complete search history.

(56) References Cited

U.S. PATENT DOCUMENTS

| | | | |
|---|---|---|---|
| 4,154,114 A * | 5/1979 | Katz et al. ................... 73/629 |
| 6,144,757 A * | 11/2000 | Fukuzumi ................... 382/124 |
| 6,529,754 B2 * | 3/2003 | Kondo ......................... 600/344 |
| 6,898,299 B1 * | 5/2005 | Brooks ........................ 382/115 |
| 7,236,616 B1 * | 6/2007 | Scott ........................... 382/124 |
| 7,366,332 B2 * | 4/2008 | Shimamura et al. ......... 382/124 |
| 7,508,963 B2 * | 3/2009 | Shimamura et al. ......... 382/124 |
| 7,548,636 B2 * | 6/2009 | Shimamura et al. ......... 382/115 |
| 2002/0151775 A1 * | 10/2002 | Kondo ......................... 600/344 |
| 2003/0135097 A1 * | 7/2003 | Wiederhold et al. ......... 600/301 |
| 2005/0244038 A1 * | 11/2005 | Benkley, III ................ 382/126 |
| 2005/0259850 A1 * | 11/2005 | Shimamura et al. ......... 382/124 |
| 2006/0034493 A1 * | 2/2006 | Shimamura et al. ......... 382/115 |
| 2006/0038689 A1 * | 2/2006 | Ikegami et al. ............... 340/575 |
| 2007/0195989 A1 * | 8/2007 | Tsubata et al. .............. 382/100 |

* cited by examiner

*Primary Examiner*—Daniel G Mariam
*Assistant Examiner*—Aklilu K Woldemariam
(74) *Attorney, Agent, or Firm*—Adams & Wilks

(57) ABSTRACT

A biometric information measuring apparatus has a biometric signal detecting portion that detects a biometric signal. A control section calculates biometric information based on the detected biometric signal by nullifying an amplitude of the detected biometric signal corresponding to a noise portion of the detected biometric signal when the nullified amplitude does not satisfy a predetermined threshold value.

19 Claims, 6 Drawing Sheets

US 7,885,432 B2

BIOMETRIC INFORMATION MEASURING APPARATUS

BACKGROUND OF THE INVENTION

1. Field of the Invention

The present invention relates to a biometric information measuring apparatus for measuring biometric information of pulse, heart beat or the like.

2. Description of the Prior Art

In a background art, there has been developed a biometric information measuring apparatus for detecting a biometric signal of a person, such as a pulse signal, a heart beat signal or the like, and for measuring biometric information in correspondence with the biometric signal, such as a pulse number, a heartbeat number or the like per unit time.

When the biometric signal is detected, noise by physical movement or the like of a measured person is brought about and therefore, a measurement error produced by the noise or the like needs to be restrained.

In a biometric information measuring apparatus of a pulsimeter, a heart beat meter or the like of a background art, when the pulse number or the heart beat number is calculated from the pulse signal or the heart beat signal, fast Fourier transformation (FFT) is utilized (refer to, for example, JP-A-2003-265441).

However, according to the invention described in JP-A-2003-265441, when the signal waveform is disturbed by the physical movement or the like, as a result of FFT processing, other than a base line intended to be calculated inherently, a noise baseline proximate to a direct current component emerges at a high level and accurate measurement becomes difficult.

In order to prevent this, as in the invention described in JP-A-2003-265422, a high degree algorism needs to be used and therefore, there poses a problem that the processing becomes complicated.

The invention has been carried out in view of the above-described problem and it is an object of the present invention to be able to measure biometric information utilizing a highly accurate and simple apparatus and process.

SUMMARY OF THE INVENTION

According to the invention, there is provided a biometric information measuring apparatus characterized in a biometric information measuring apparatus including biometric signal detecting means for detecting a biometric signal provided from the human body, biometric information outputting means for outputting biometric information, and controlling means for calculating the biometric information based on the biometric signal detected by the biometric signal detecting means and controlling the biometric information outputting means to output the biometric information, where, in the controlling means calculates the biometric information by using a biometric signal other than a noise portion included in the biometric signal within a predetermined time period and controlling the biometric information outputting means to output the biometric information.

The biometric signal detecting means detects the biometric signal provided from the human body. The controlling means calculates the biometric information by using the biometric signal other than the noise portion included in the biometric signal within the predetermined time period and controls the biometric information outputting means to output the biometric information. The biometric information outputting means outputs the biometric information.

Here, there may be constructed a constitution in which the controlling means uses a predetermined signal level with regard to the biometric signal as a threshold and calculates the biometric information by using a signal satisfying the threshold as the biometric signal other than the noise portion. Further, there may be constructed a constitution in which the threshold constitutes a first threshold with regard to a signal level in a first direction and constitutes a second threshold with regard to a signal level in a second direction of a direction inverse to the first direction, and the first threshold and the second threshold are constituted by being set to values different from each other, herein the controlling means constitutes a biometric signal satisfying the two thresholds as the biometric signal other than the noise portion and calculates the biometric information by using the biometric signal.

Further, there may be constructed a constitution in which the controlling means is constituted by including amplifying means for amplifying to output the biometric signal detected by the biometric signal detecting means, and gain controlling means for restraining an output signal level of the amplifying means within a predetermined range by controlling a gain of the amplifying means based on an output signal of the amplifying means, the gain controlling means controls the gain of the amplifying means based on a plurality of newest biometric signals included in the predetermined time period, and the controlling means calculates the biometric information based on the biometric signal other than the noise portion in signals outputted from the amplifying means.

Further, there may be constructed a constitution in which the controlling means calculates the biometric information by subjecting the biometric signal other than the noise portion to an FFT processing.

Further, there may be constructed a constitution in which the controlling means calculates the biometric information by calculating a number of biometric signals exceeding a predetermined signal level in the biometric signals other than the noise portion.

Further, there may be constructed a constitution in which the biometric signal is a pulse signal or a heart beat signal, and the biometric information is a pulse number or a heart beat number per unit time in correspondence with the biometric signal.

Further, there may be constructed a constitution in which the biometric information outputting means is displaying means.

BRIEF DESCRIPTION OF THE DRAWINGS

A preferred form of the present invention is illustrated in the accompanying drawings in which.

DETAILED DESCRIPTION OF THE PREFERRED EMBODIMENTS

An explanation will be given of a biometric information measuring apparatus according to the embodiment of the invention as follows. Further, according to following respective embodiments, an explanation will be given by taking an example of a pulsimeter as a biometric information measuring apparatus.

Figure 1:
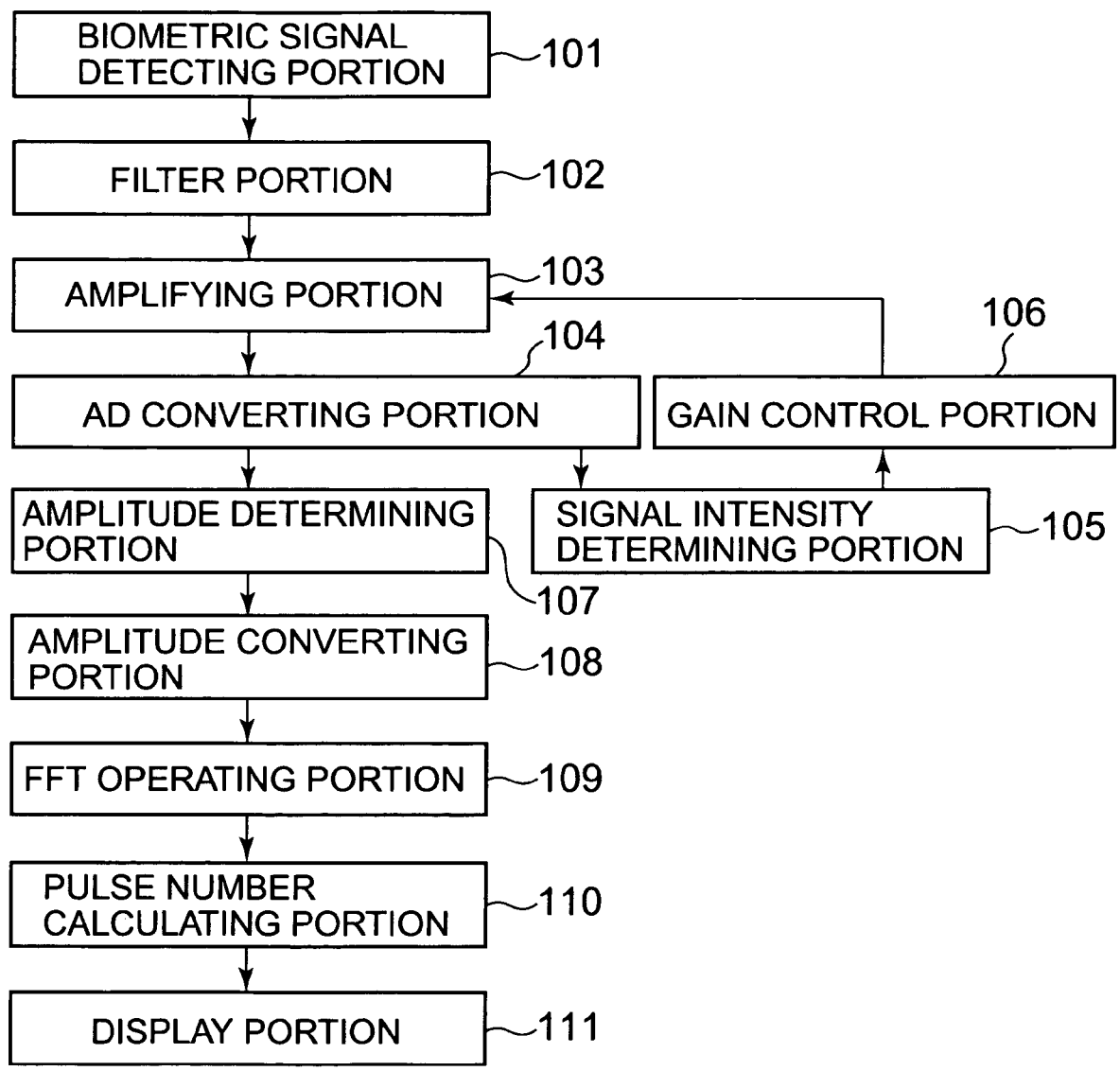
FIG. 1 is a block diagram of a pulsimeter according to a first embodiment of the invention.

FIG. 1 is a block diagram of a pulsimeter according to a first embodiment of the invention. The pulsimeter is provided with a wristwatch type outlook and is used by being mounted to the arm of a measured person such that pulse can be detected from the finger or the wrist.

In FIG. 1, the pulsimeter includes a biometric signal detecting portion 101 for detecting to output pulse constituting a biometric signal from the finger, the wrist or the like of the measured person, a filter portion 102 constituted by a low pass filter or a band pass filter for removing high frequency noise in the biometric signal from the biometric signal detecting portion 101, an amplifying portion 103 for amplifying the biometric signal from the filter portion 102, an analog/digital (AD) converting portion 104 for converting an output signal from the amplifying portion 103 from an analog signal to a digital signal, a signal intensity determining portion 105 for determining an intensity of an output signal of the AD converting portion 104 and outputting a signal in accordance with the intensity, a gain control portion 106 for controlling a gain of the amplifying portion 103 such that the signal at a pertinent level is outputted from the amplifying portion 103 based on a signal from the signal intensity determining portion 105, an amplitude determining portion 107 for determining an amplitude of the output signal by comparing the output signal of the AD converting portion 104 with a predetermined threshold, an amplitude converting portion 108 for converting an amplitude of an output signal of the AD converting portion 104 into a predetermined value based on a result of determination by the amplitude determining portion 107, an FFT operating portion 109 for subjecting the biometric signal of pulse or the like outputted from the amplitude converting portion 108 to FFT processing, a pulse number calculating portion 110 for calculating biometric information of a pulse number or the like in correspondence with the biometric signal based on an output signal of the FFT operating portion 109, and a display portion 111 for displaying biometric information of a pulse number or the like calculated by the pulse number calculating portion 110.

Here, the biometric information detecting portion 101 constitutes biometric information detecting means, the display portion 111 constitutes biometric information outputting means. Controlling means is constituted by the filter portion 102, the amplifying portion 103 constituting amplifying means, the AD converting portion 104, the signal intensity determining portion 105, the gain control portion 106, the amplitude determining portion 107, the amplitude converting portion 108, the FFT operating portion 109 and the pulse number calculating portion 110. The signal intensity determining portion 105 and the gain control portion 106 constitute gain controlling means for restraining an output signal level of the amplifying portion 103 to a predetermined range by controlling the gain of the amplifying portion 103 based on the output signal of the amplifying portion 103. AGC amplifying means is constituted by the amplifying portion 103, the AD converting portion 104, the signal intensity determining portion 105 and the gain control portion 106. Further, calculating means is constituted by the FFT operating portion 109 and the pulse number calculating portion 110.

Figure 2:
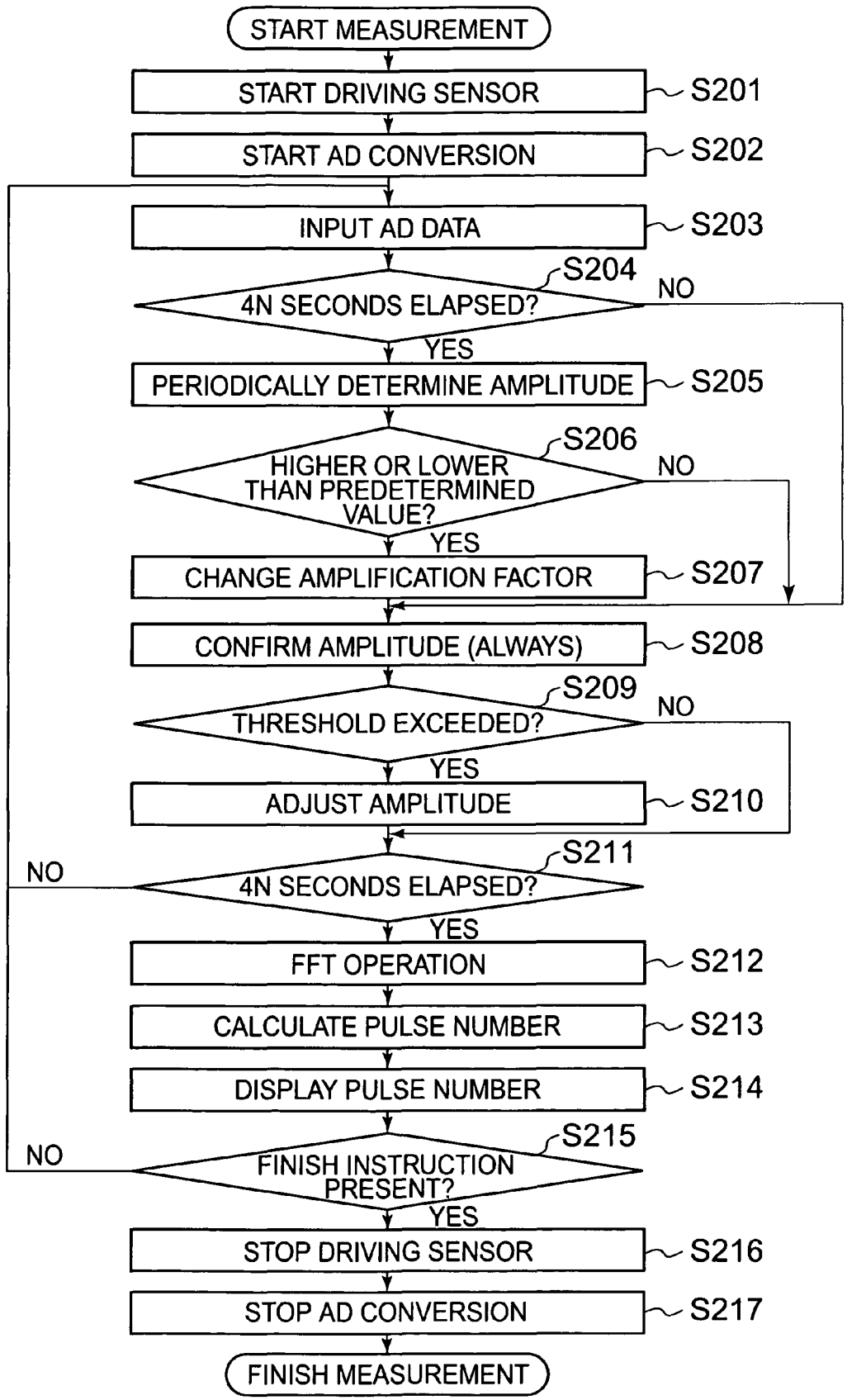
FIG. 2 is a flowchart showing a processing according to the first embodiment of the invention.

FIG. 2 is a flowchart showing operation of the first embodiment. Further, FIG. 3 through FIG. 6 are diagrams for explaining operation of the first embodiment.

A detailed explanation will be given of an operation of, the first embodiment by using FIG. 1 and FIG. 2 and pertinently in reference to FIG. 3 through FIG. 6 as follows.

First, when pulse measuring operation of the pulse detecting apparatus is started, the biometric signal detecting portion 101 starts operation of detecting the pulse signal constituting the biometric signal of the measured person to output the detected pulse signal (step S201 of FIG. 2: start driving sensor).

The pulse signal outputted from the biometric signal detecting portion 101 is reduced in high frequency noise by the filter portion 102, amplified by the amplifying portion 103, started to be converted from an analog signal to a digital signal by being subjected to AD conversion by the AD converting portion 104 (step S202), and the analog style pulse signal is converted into the digital style to be inputted (step S203).

Further, the signal intensity determining portion 105 determines the intensity of the pulse signal by comparing a value related to a plurality of newest pulse signal data supplied from the AD converting portion 104 in a predetermined time period (for example, an average value of a predetermined number of newest pulse data) and a predetermined reference value, and outputs a signal in accordance with the result of determination to the gain control portion 106. The gain control portion 106 controls a gain of the amplifying portion 103 such that the pulse signal outputted from the amplifying portion 103 is at a level of a predetermined range based on the signal from the signal intensity determining portion 105.

Figure 3:
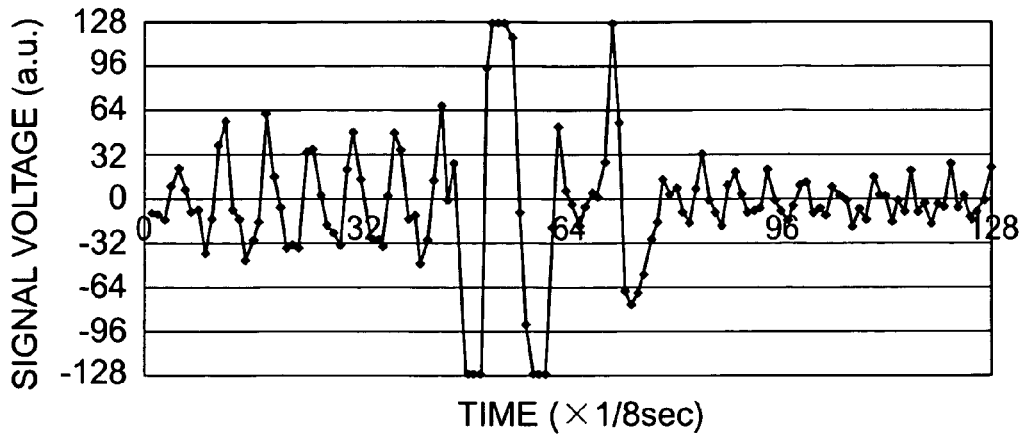
FIG. 3 is a diagram for explaining operation of a pulsimeter according to the first embodiment of the invention.

FIG. 3 is a diagram showing the pulse signal data outputted from the AD converting portion 104. A sampling frequency of the AD converting portion is 8 Hz, and FIG. 3 shows 128 pieces (amount of 16 seconds) of the pulse signal data.

Operation of controlling the gain of the amplifying portion 103 is not carried out at each time of varying an output level thereof but is carried out based on the plurality of newest pulse signal data included in the predetermined time period and therefore, a response of the operation of controlling the gain is retarded relative to a variation in the output of the amplifying portion 103. Therefore, in FIG. 3, at a periphery of a center portion of a time axis, a dynamic range of the amplifying portion 103 is exceeded and therefore, a waveform saturating a signal voltage is constituted. With regard to the pulse data thereafter, the amplitude is reduced by an effect of the gain controlling operation.

Next, after an elapse of a predetermined time period (according to the embodiment, 4n (n is positive integer) seconds), that is, after the AD converting portion 104 inputs the pulse signal of the digital style for 4n seconds (step S204), the signal intensity determining portion 105 carries out determination of the amplitude (periodic amplitude determination) of the inputted pulse signal (step S205). Here, the predetermined time period is constituted by a multiplication factor of integer (n) of 4 for facilitating to carry out FFT processing which is carried out at a later stage.

When the amplitude is out of the predetermined reference value (higher or lower than the predetermined value) as a result of determining the amplitude by the signal intensity determining portion 105 (step S206), after the gain control portion 106 changes the gain of the amplifying portion 103 such that the level of the pulse signal falls in the predetermined range (step S207), the amplitude determining portion 107 confirm the amplitude of the pulse signal outputted from the AD converting portion 104 (step S208). Further, at step S206, when the amplitude is within the predetermined reference value, the gain is not changed by the amplifying portion 103 and the operation proceeds to step S208.

Next, the amplitude determining portion 107 determines whether the amplitude of the pulse signal outputted from the AD converting portion 104 satisfies a predetermined threshold (step S209), when it is determined that the threshold is not satisfied, it is determined that noise by physical movement or the like is included, the amplitude converting portion 108 adjusts the amplitude of the pulse signal outputted from the AD converting portion 104 (step S210).

Figure 5:
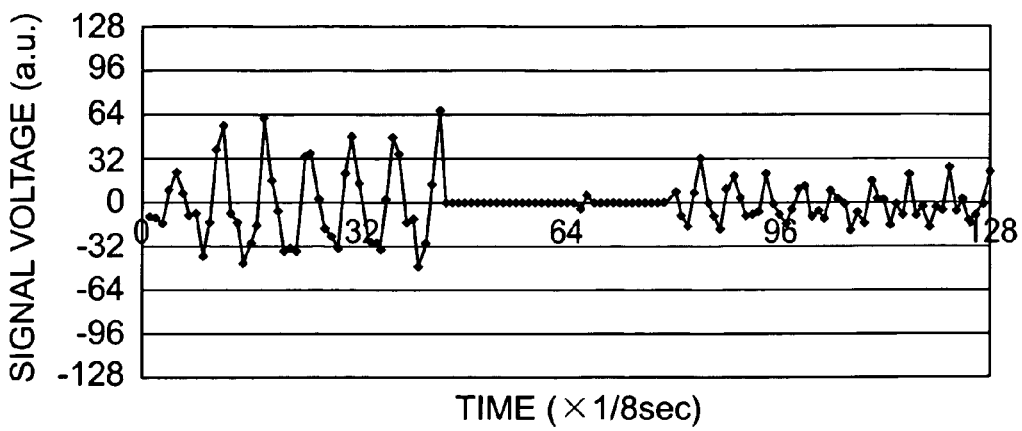
FIG. 5 is a diagram for explaining the operation of the pulsimeter according to the first embodiment of the invention.

FIG. 5 shows the pulse data after the amplitude converting portion 108 adjusts the amplitude of the pulse data of FIG. 3. According to the example of FIG. 5, a threshold (first threshold) in a first direction (positive direction in the example) is constituted by 96 (arbitrary unit), a threshold (second threshold) in a direction reverse to the first direction (negative direction in the example) is constituted by 64 (arbitrary unit) to thereby constitute the two thresholds to differ from each other, a signal outside of a range of the first threshold and the second threshold is determined as a signal of a noise portion which does not satisfy the threshold, and amplitudes of respective signals included in the noise portion and signals of 1 second frontward and rearward from the respective signals are nullified.

Next, the FFT operating portion 109 determines whether a predetermined time period (4n seconds according to the embodiment) has elapsed (step S211).

At step S211, when the predetermined time period has not elapsed, the operation returns to step S203, when the predetermined time period has elapsed, the FFT operating portion 109 carries out the FFT processing based on the pulse signal from the amplitude converting portion 108 (step S212), and the pulse number calculating portion 110 carries out a processing of calculating the pulse number (step 213). Thereby, the FFT operating portion 109 calculates the biometric information by using the biometric signal other than the noise portion included in the biometric signal within the predetermined time period.

Figure 4:
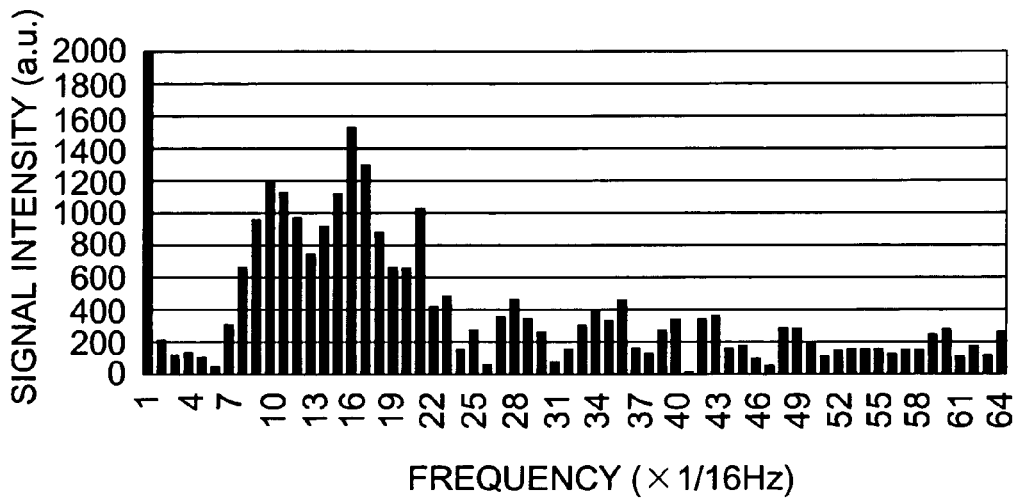
FIG. 4 is a diagram for explaining the operation of the pulsimeter according to the first embodiment of the invention.

FIG. 4 is a diagram showing a result of carrying out the FFT processing by the FFT operating portion 109 based on the pulse data shown in FIG. 3 in which the amplitude has not been adjusted.

Figure 6:
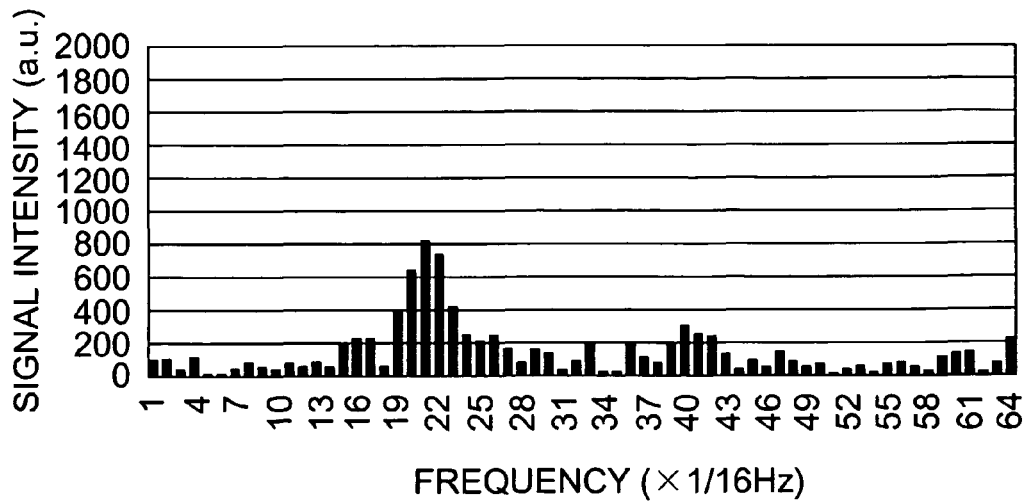
FIG. 6 is a diagram for explaining the operation of the pulsimeter according to the first embodiment of the invention.

In contrast thereto, FIG. 6 shows a diagram showing a result of carrying out the FFT processing by the FFT operating portion 109 based on the pulse data shown in FIG. 5 in which the amplitude has been adjusted.

As is apparent by comparing FIG. 4 and FIG. 6, in FIG. 6, by adjusting the amplitude, the noise by the physical movement or the like is reduced and the accurate pulse can be calculated. According to the example of FIG. 6, the heart beat number is about 80 beats.

The display portion 111 displays the pulse number calculated by the pulse number calculating portion 110 (step S214).

Thereafter, when a finish instruction is not inputted by operating an operating portion (not illustrated) of the pulsimeter, the operation returns to step S203 to repeat the above-described processings (step S215).

On the other hand, when the finish instruction is inputted at step S215, the biometric signal detecting portion is stopped to be driven (step S216), the AD converting operation by the AD converting portion 104 is stopped (step S217), and the operation is finished.

As described above, according to the first embodiment, the biometric information is calculated by using the biometric signal other than the noise portion included in the biometric signal within the predetermined time period and therefore, the pulse can be measured highly accurately by a simple processing.

Further, there is constructed a constitution in which the predetermined signal level is used as the threshold for the biometric signal, the biometric information is calculated by using the signal satisfying the threshold of the biometric signal at other than the noise portion, there is constructed a constitution in which the threshold in the first direction and the threshold in the second direction of the direction inverse to the first direction are set to values different from each other in accordance with a characteristic of the pulse signal in which the pulse signal is large in the first direction and is small in the second direction inverse thereto, the biometric signal satisfying the two thresholds is made to constitute the biometric signal at other than the noise portion, and the biometric information is calculated by using the biometric signal and therefore, the pulse can be measured highly accurately.

Further, the gain of the amplifying portion 103 is controlled based on the plurality of newest biometric signals included in the predetermined time period and therefore, gradual and pertinent gain controlling operation is carried out without excessively in response to external noise and the pulse can be measured further highly accurately.

Further, the pulse number can be measured highly accurately by subjecting the biometric signal at other than the noise portion to the FFT processing.

Figure 7:
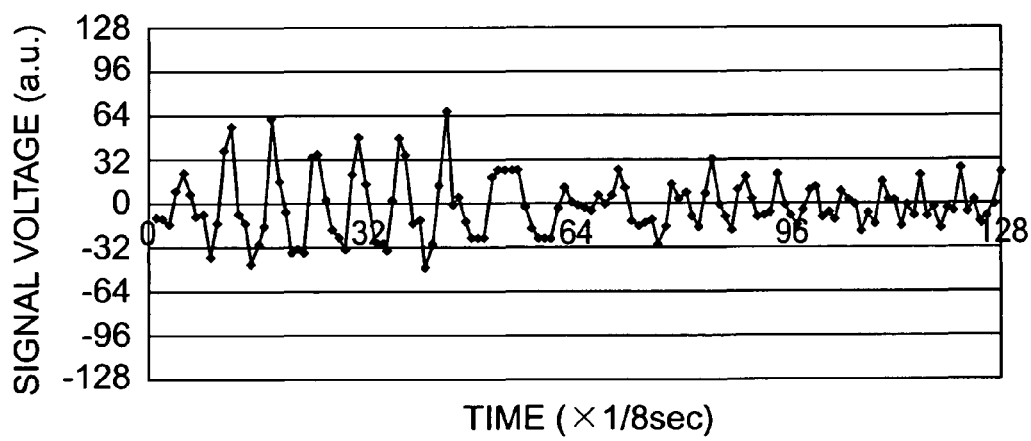
FIG. 7 is a diagram for explaining operation of a pulsimeter according to a second embodiment of the invention.

FIG. 7 is a diagram showing pulse data after adjusting an amplitude thereof in a pulsimeter according to a second embodiment of the invention. The second embodiment is the same as the first embodiment in a block diagram and a flowchart thereof and differs from the first embodiment in that thresholds of the amplitude determining portion 107 differs therefrom.

That is, in an example of FIG. 7, the thresholds are constituted such that two thresholds as an upper limit value and a lower limit value of a dynamic range are the same, a signal out of the range of the thresholds is determined as a noise portion which does not satisfy the thresholds, and amplitudes of respective signals included in the noise portion and signals 1 second frontward and rearward from the respective signals (here, a number of data is 2 pieces frontward, 5 pieces rearward) are reduced to 20% thereof.

Figure 8:
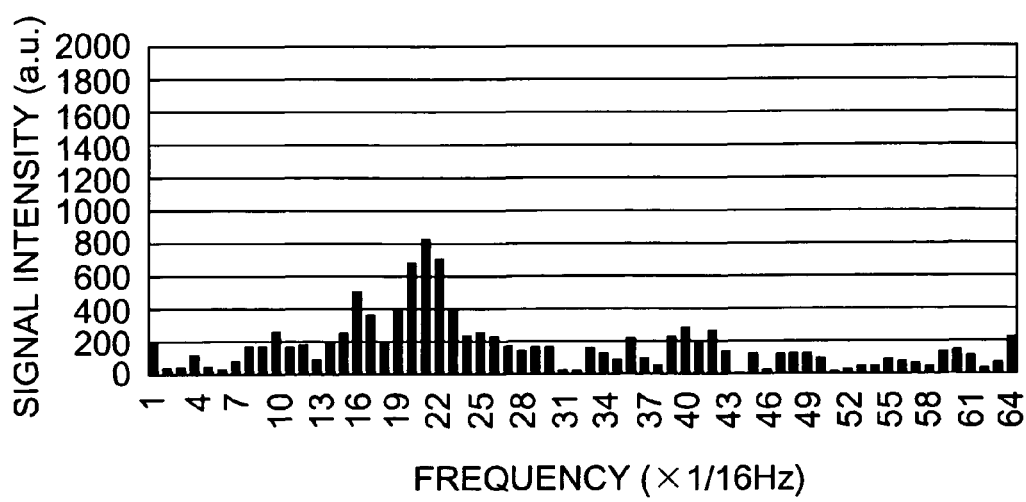
FIG. 8 is a diagram for explaining the operation of the pulsimeter according to the second embodiment of the invention.

FIG. 8 is a diagram showing a result of carrying out the FFT processing by the FFT calculating portion 109 based on pulse data after adjusting the amplitudes shown in FIG. 7.

As is apparent by comparing FIG. 4 and FIG. 8, in FIG. 8, the noise by the physical movement or the like is restrained by adjusting the amplitudes and therefore, when subjected to the FFT processing, a measurement error by the noise can be restrained and the pulse number can accurately be calculated.

Figure 9:
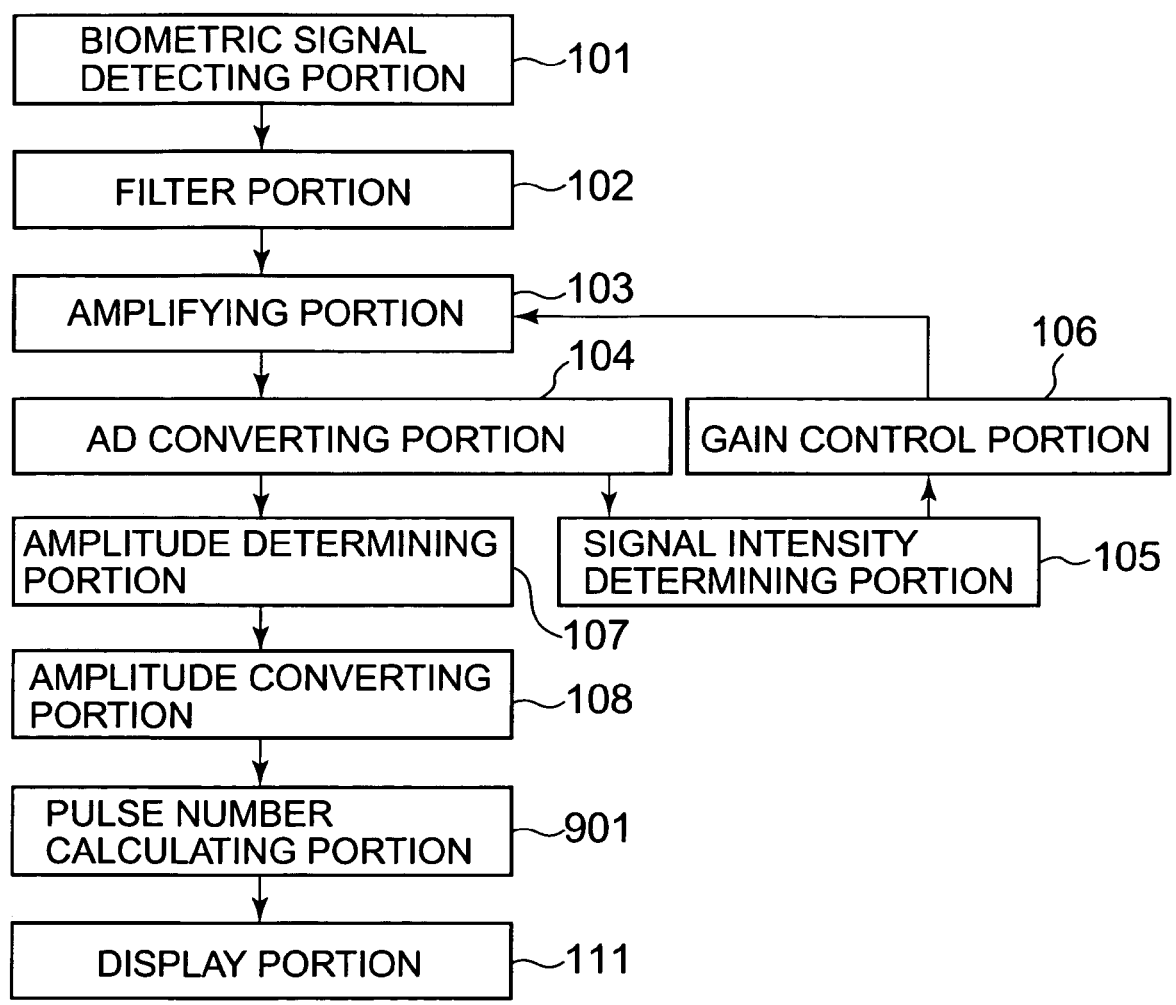
FIG. 9 is a block diagram of a pulsimeter according to a third embodiment of the invention.

FIG. 9 is a block diagram of the pulsimeter according to a third embodiment of the invention, the portions the same as those of FIG. 1 are attached with the same notations.

Figure 10:
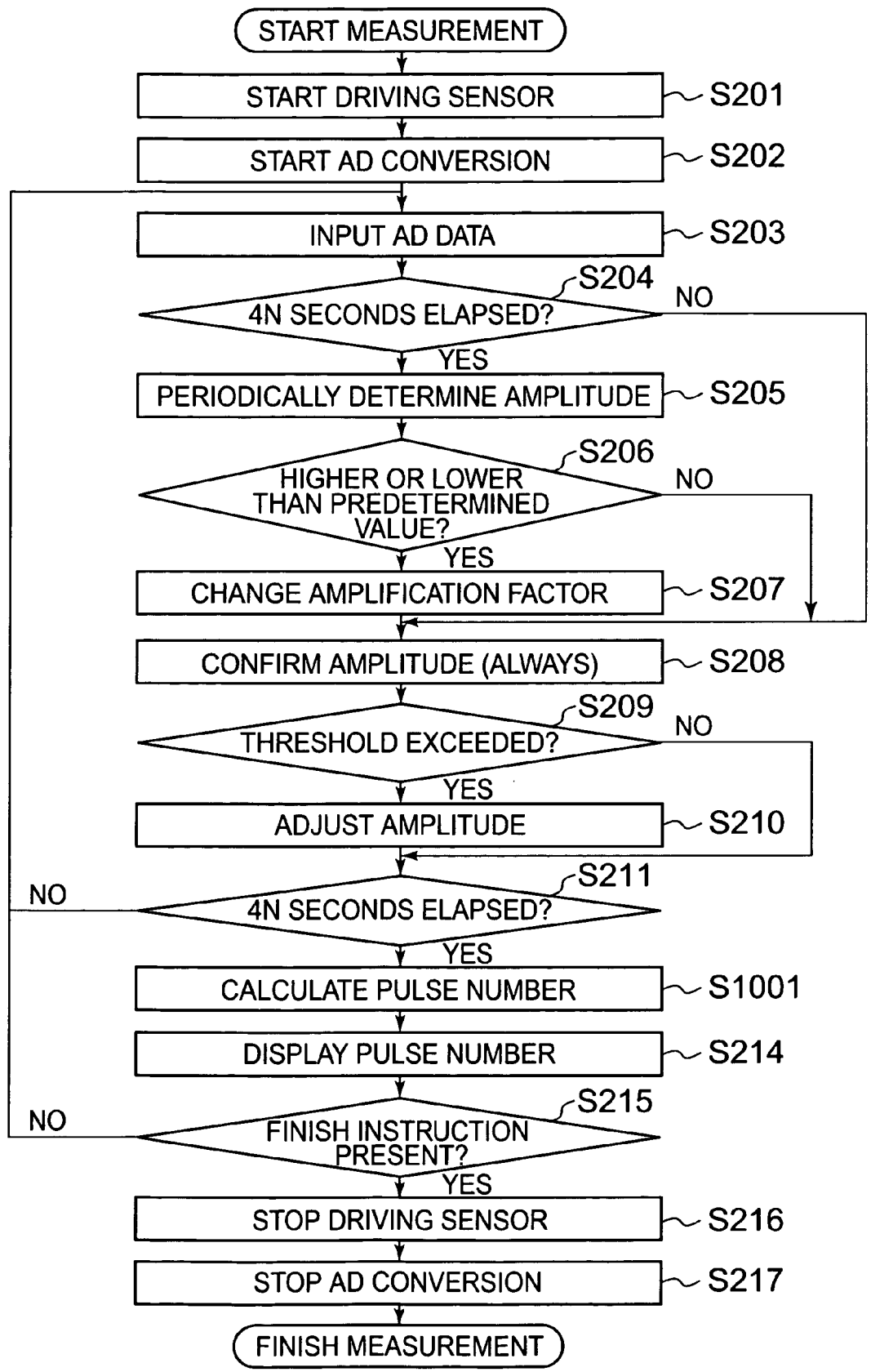
FIG. 10 is a flowchart showing a processing according to the third embodiment of the invention.

Further, FIG. 10 is a flowchart showing a processing according to the third embodiment and portions the same as those of FIG. 2 are attached with the same notations.

A point of the third embodiment which differs from the first embodiment resides in that the third embodiment is constituted to calculate the biometric information by calculating a number of pulse signals exceeding a predetermined signal level in pulse signals other than a noise portion included in pulse signals in a predetermined time period without carrying out the FFT processing.

An explanation will be given of operation of a portion of the third embodiment which differs from the first embodiment in reference to FIG. 9 and FIG. 10 as follows.

In FIG. 9 and FIG. 10, the amplitude converting portion 108 determines pulse signals out of predetermined thresholds as signals including noise of physical movement or the like to adjust to amplitudes within the predetermined range as shown by, for example, FIG. 5 or FIG. 7 (step S210).

Next, it is determined whether a predetermined time period (according to the embodiment, 4n seconds) has elapsed (step S211).

At step S211, when the predetermined time period has elapsed, a pulse number calculating portion 901 carries out a processing of calculating a pulse number (step S1001).

Next, the display portion 111 displays the pulse number calculated by the pulse number calculating portion 901 (step S214) and processings similar to those of the first embodiment are carried out as follows.

As described above, also according to the third embodiment, the pulse number calculating portion 901 calculates the biometric information by using the pulse signals other than the noise portion included in the pulse signal in the predetermined time period, in this case, particularly, the biometric information is calculated by calculating a number of the pulse signals exceeding the predetermined thresholds in the pulse signal other than the noise portion.

Therefore, the measurement error by the noise of the physical movement or the like can be restrained and the pulse number can accurately be calculated by carrying out a simple processing without being subjected to a complicated processing as in FFT.

Further, although according to the respective embodiments, an explanation has been given by taking an example of the pulse as the biometric information, there can be constructed a constitution of measuring biometric information of the human body which is periodically generated such as heart beat, walk or the like.

According to the invention, the biometric information of the pulse, the heart beat or the like can be measured highly accurately by a simple processing.

The invention is applicable not only to a pulsimeter but also to a biometric information measuring apparatus for measuring biometric information of pulse, heart beat, walk or the like of a person such as a heart beat meter, a walk number meter or the like.

What is claimed is:

1. A biometric information measuring apparatus comprising:
    biometric signal detecting means for detecting a biometric signal from a human body;
    biometric information outputting means for outputting biometric information corresponding to the detected biometric signal; and
    controlling means for calculating the biometric information and for controlling the biometric information outputting means to output the calculated biometric information, the controlling means calculating the biometric information using the biometric signal detected within a predetermined time period other than a noise portion that is included in the detected biometric signal and that does not satisfy a threshold, with amplitudes of respective signals included in the noise portion and signals one second frontward and rearward from the respective signals being reduced or nullified.

2. A biometric information measuring apparatus according to claim 1; wherein the threshold is a predetermined signal level of the detected biometric signal.

3. A biometric information measuring apparatus according to claim 1; wherein the threshold comprises a first threshold in a first direction and a second threshold different from the first threshold and in a second direction reverse to the first direction, the signals included in the noise portion being outside of a range of the first and second thresholds.

4. A biometric information measuring apparatus according to claim 1; wherein the controlling means comprises amplifying means for amplifying the biometric signal detected by the biometric signal detecting means, and gain controlling means for restraining an output signal level of the amplifying means within a predetermined range by controlling a gain of the amplifying means based on an output signal of the amplifying means and based on a plurality of newest biometric signals included in the predetermined time period.

5. A biometric information measuring apparatus according to claim 1; wherein the controlling means calculates the biometric information by subjecting the detected biometric signal other than the signals included in the noise portion to fast Fourier transform (FFT) processing.

6. A biometric information measuring apparatus according to claim 1; wherein the detected biometric signal is a pulse signal or a heart beat signal, and the biometric information is a pulse number or a heart beat number per unit time corresponding to the detected biometric signal.

7. A biometric information measuring apparatus according to claim 6; wherein the biometric information outputting means comprises displaying means for displaying the calculated biometric information.

8. A biometric information measuring apparatus comprising: a biometric signal detecting portion that detects a biometric signal; and a control section that calculates biometric information using the detected biometric signal other than a noise portion that is included in the detected biometric signal and that does not satisfy a threshold, with amplitudes of respective signals included in the noise portion and signals one second frontward and rearward from the respective signals being reduced or nullified.

9. A biometric information measuring apparatus according to claim 8; further comprising a biometric information outputting portion that is controlled by the control section to output the calculated biometric information.

10. A biometric information measuring apparatus according to claim 9; wherein the biometric information outputting portion comprises a display portion that displays the calculated biometric information.

11. A biometric information measuring apparatus according to claim 8; wherein the detected biometric signal is a pulse signal or a heart beat signal, and the calculated biometric information is a pulse number or a heart beat number per unit time corresponding to the detected biometric signal.

12. A biometric information measuring apparatus according to claim 8; wherein the threshold is a predetermined signal level of the detected biometric signal.

13. A biometric information measuring apparatus according to claim 8; wherein the threshold comprises a first threshold in a first direction and a second threshold different from the first threshold and in a second direction reverse to the first direction, the signals included in the noise portion being outside of a range of the first and second thresholds.

14. A biometric information measuring apparatus according to claim 8; wherein the controlling section comprises an amplifying portion that amplifies the detected biometric signal and a gain control poriton that restrains an output signal level of the amplifying portion within a predetermined range by controlling a gain of the amplifying portion based on an output signal of the amplifying portion.

15. A biometric information measuring apparatus according to claim 8; wherein the controlling section calculates the biometric information by subjecting the detected biometric signal other than the signals included in the noise portion to fast Fourier transform (FFT) processing.

16. A biometric information measuring apparatus according to claim 1; wherein the controlling means calculates the biometric information such that the amplitudes of respective signals included in the noise portion and signals 1 second frontward and rearward from the respective signals are nullified.

17. A biometric information measuring apparatus according to claim 1; wherein the controlling means calculates the biometric information such that the amplitudes of respective signals included in the noise portion and signals 1 second frontward and rearward from the respective signals are reduced to 20% thereof.

18. A biometric information measuring apparatus according to claim 8; wherein the control section calculates the biometric information such that the amplitudes of respective signals included in the noise portion and signals 1 second frontward and rearward from the respective signals are nullified.

19. A biometric information measuring apparatus according to claim 8; wherein the control section calculates the biometric information such that the amplitudes of respective signals included in the noise portion and signals 1 second frontward and rearward from the respective signals are reduced to 20% thereof.

* * * * *